US006033629A

United States Patent [19]
Friederick et al.

[11] Patent Number: 6,033,629
[45] Date of Patent: Mar. 7, 2000

[54] ASHING FURNACE

[75] Inventors: Mark J. Friederick; Steven C. Peake, both of Dubuque, Iowa

[73] Assignee: Barnstead/Thermolyne Corporation, Dubuque, Iowa

[21] Appl. No.: 09/040,572

[22] Filed: Mar. 18, 1998

[51] Int. Cl.[7] .................................................. G01N 31/12
[52] U.S. Cl. ............................ 422/78; 110/210; 110/211; 110/216; 110/345; 422/99; 422/101; 422/104
[58] Field of Search .............................. 422/78, 99, 101, 422/102, 104; 436/155, 160; 110/210, 211, 216, 345

[56] References Cited

U.S. PATENT DOCUMENTS

| 2,962,987 | 12/1960 | Hebert et al. . |
| 3,496,890 | 2/1970 | LaRue . |
| 3,880,143 | 4/1975 | Hart et al. . |
| 4,269,592 | 5/1981 | Benton et al. . |
| 4,270,898 | 6/1981 | Kelly . |
| 4,449,921 | 5/1984 | Catallo . |
| 4,878,839 | 11/1989 | Wunning . |
| 5,251,564 | 10/1993 | Rim et al. . |
| 5,558,029 | 9/1996 | Peake . |

*Primary Examiner*—Jan Ludlow
*Attorney, Agent, or Firm*—Wood, Herron & Evans, L.L.P.

[57] ABSTRACT

A furnace includes an enclosure and a hearth plate within the enclosure for supporting combustible material. The furnace further includes a first heater element adjacent the hearth plate for initial combustion of the combustible material, a filter disposed above the hearth plate for filtering uncombusted products of combustion of the combustible material, and a second heater element adjacent the filter for final combustion of the uncombusted products of combustion filtered by the filter. A filter bypass path has an inlet located in a lower portion of the enclosure and an outlet located between the filter and the second heater.

29 Claims, 2 Drawing Sheets

ASHING FURNACE

BACKGROUND OF THE INVENTION

This invention relates generally to furnaces, and more particularly, to furnaces for ashing or burnout applications to determine the weight loss of a specimen as one or more of its constituents are burned off.

So-called ashing furnaces have been used to determine the weight loss of a specimen as one or more of its constituents are burned off. A typical ashing furnace includes an enclosure, a heating element for applying heat to and combusting the combustible portion of the material within the enclosure, and a weigh scales for weighing the specimen before, during and after one or more of its combustible constituents are burned off. Such an ashing furnace is described in U.S. Pat. No. 5,558,029, for Ashing Furnace and Method, which patent is assigned to the same assignee as the present invention and is hereby incorporated herein by reference as if fully set forth herein in its entirety.

One application of ashing furnaces is in the area of asphalt ashing where it is desired to determine the binder content in asphalt by burning the binder off from a sample of asphalt. Asphalt typically is comprised of 93½% by weight rock, sand and other particulate matter, for example rock dust, 6% light crude (binder) and ½% other matter. The sample of asphalt is weighed before combustion and after combustion. Combustion occurs at approximately 1,000° F., a temperature at which the 93½% by weight rock, sand and particulate matter is inert. The sample is weighed after its weight rate of change with respect to time is approximately zero (i.e. weight change stabilizes), and the postcombustion weight is compared to the precombustion weight to determine the weight of the binder burned off and thus contained within the starting sample.

One drawback of conventional ashing furnaces is that under some circumstances, initial ignition of the load may be slow and inconsistent. At the start of a cycle, the load is not at the desired combustion temperature, and therefore, excessive uncombusted products, for example, smoke, soot and ash are produced. The excess uncombusted materials may partially blind or clog the filter in the exhaust path. Clogging the filter reduces flow through the filter and a positive pressure can be created within the main furnace chamber. That positive pressure may then result in smoke, soot or ash being expelled from the furnace through the air intake or through other openings, for example, around the perimeter of an excess door to a furnace. It is believed that the blockage of the air intake by the uncombusted materials reduces oxygen available for combustion, and therefore, combustion of the load is diminished. The production of uncombusted materials is likewise diminished and the filter, which is heated to a temperature of 750° C.–900° C., will begin combusting the uncombusted materials clogging its input. When those materials have combusted to a size that they may pass through the filter, the filter in essence cleans itself and a normal gas and air flow resumes through the furnace. As the combustion of the load increases and the load temperature rises, excessive smoke, soot and ash may again be produced thereby reducing flow through the filter, and the above-described cycle may continue over a period of time from 5–30 minutes until the combustion achieves a state permitting flow through the filter. Such an initial erratic combustion cycle is often dependent on the size of the load, its asphalt concentration and whether the load includes a rubberized asphalt. The major disadvantage of such an erratic combustion cycle is the escape of smoke, soot, ash and other uncombusted materials into the environment around the ashing furnace. The existence of such uncombusted materials in the environment surrounding the furnace is discomforting and potentially irritating to personnel and may make such areas temporarily unusable.

It is therefore an object of the present invention to provide an ashing furnace which reduces the discharge of uncombusted products of combustion into the atmosphere.

SUMMARY OF THE INVENTION

The present invention provides an ashing furnace which during initial startup, reaches its optimum operating temperature quickly without a distracting release of smoke, soot or ash into the surrounding environment. Further, the ashing furnace of the present invention provides reduced cycle times and more complete combustion during an operating cycle. Thus, the ashing furnace of the present invention is especially useful for processing larger loads and loads which have a higher asphalt content or have a rubberized asphalt content.

According to the principals of the present invention and in accordance with the preferred embodiments, the ashing furnace of the present invention provides a furnace having a combustion chamber with a support for supporting combustible material and a first heater element adjacent the support for initial combustion of the combustible material. A filter is mounted in a filter chamber above the combustion chamber, and a second heater element is mounted in the filter chamber above the filter. A filter bypass path has an inlet located in the combustion chamber and an outlet located between the filter and the second heater element in the filter chamber.

In another embodiment, the present invention provides a method of operating an ashing furnace including providing a combustion chamber with a first heater element for burning a load of combustible material and filtering the uncombusted products of combustion to prevent their escape into the environment. The method further comprises moving the products of combustion along a bypass path around the filter in response to the filter becoming clogged and burning the products of combustion bypassing the filter.

The above furnace construction and operation has several advantages. First, if the filter should become blocked, the filter bypass path provides a path or shunt for the smoke, soot and ash which is then combusted by the second heater element so that it is not discharged directly into the surrounding environment. Second, if the filter becomes clogged, the flow of gasses through the filter bypass path facilitates the continuing flow of combustion air through the inlet channels, and hence, the combustion and temperature of the load will continue to increase at a desirable rate. That has the further advantage of the load reaching the desired combustion temperature and the furnace achieving a steady state condition in the shortest period of time. Thus, the overall cycle time for the furnace is reduced. In addition, during the steady state operation of the furnace, the filter bypass path provides combustion air directly to the filter chamber to further facilitate more complete combustion of the products of combustion passing therethrough.

These and other objects and advantages of the present invention will become more readily apparent during the following detailed description taken in conjunction with the drawings herein, in which:

DETAILED DESCRIPTION OF THE INVENTION

Figure 1:
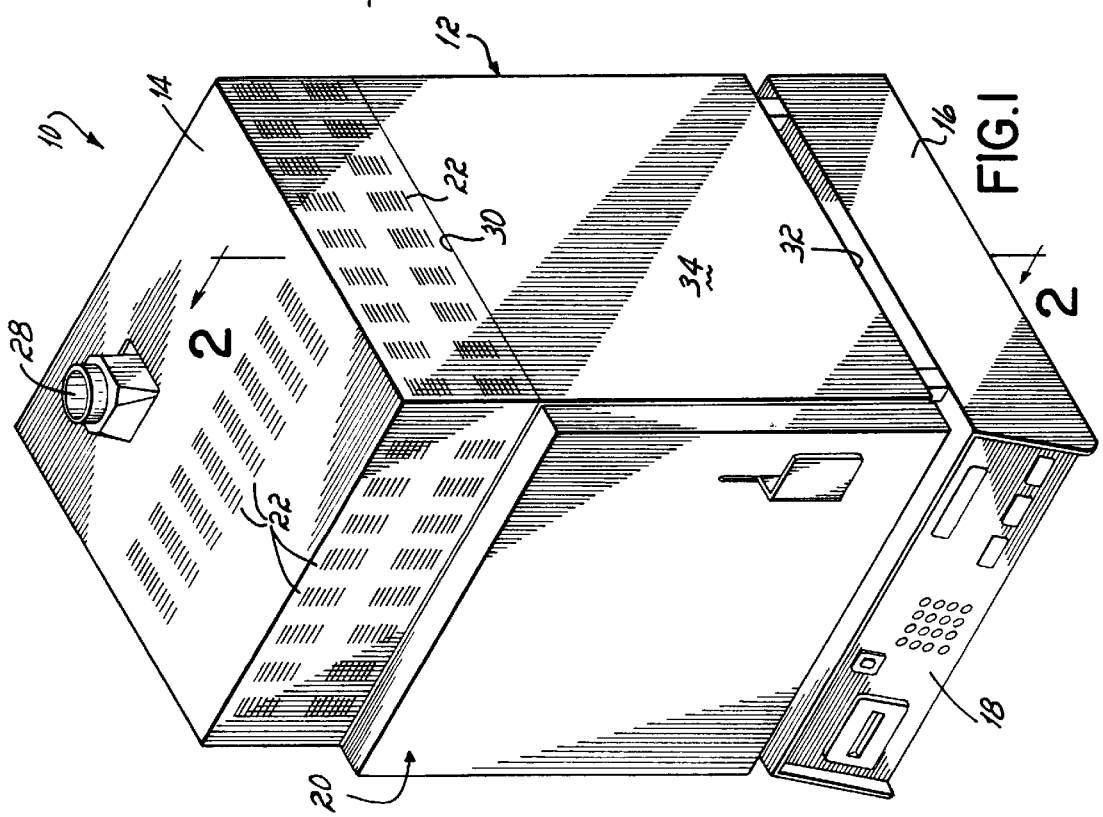
FIG. 1 is a perspective view of the ashing furnace of the present invention.

Referring first to FIG. 1, there is illustrated an ashing furnace 10 according to the principles of the present invention. The ashing furnace 10 includes an enclosure 12 having an outer blower hood 14 mounted thereatop, the enclosure 12 being supported atop a base 16 including an operator input and display panel 18 for entry of data to ashing furnace 10 and for display of weight information, and housing controller boards 19, for example, models PC859x1A and PC859x3A from Barnstead|Thermolyne, Dubuque, Iowa, for controlling the operation of ashing furnace 10. An access door 20 is provided for gaining access to the interior of enclosure 12. Outer hood 14 includes a plurality of air intake slots 22 for drawing in ambient air to an inner hood 24 which also includes a plurality of air intake slots 26. A blower 27 is mounted to inner hood 24. A discharge outlet 28 is provided on blower 27 and is vented to the atmosphere.

Figure 3:
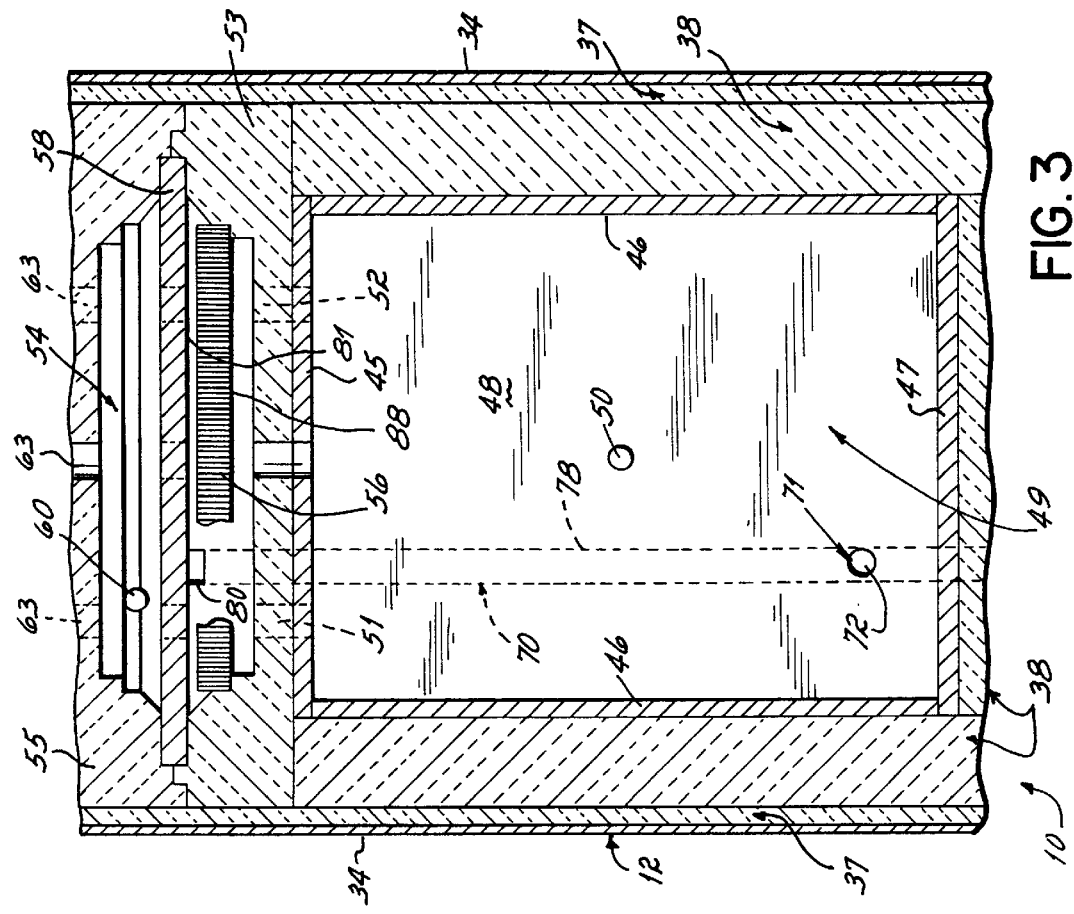
FIG. 3 is a cross-sectional view of the furnace of FIG. 1 taken along line 3—3 of FIG. 2.
Figure 2:
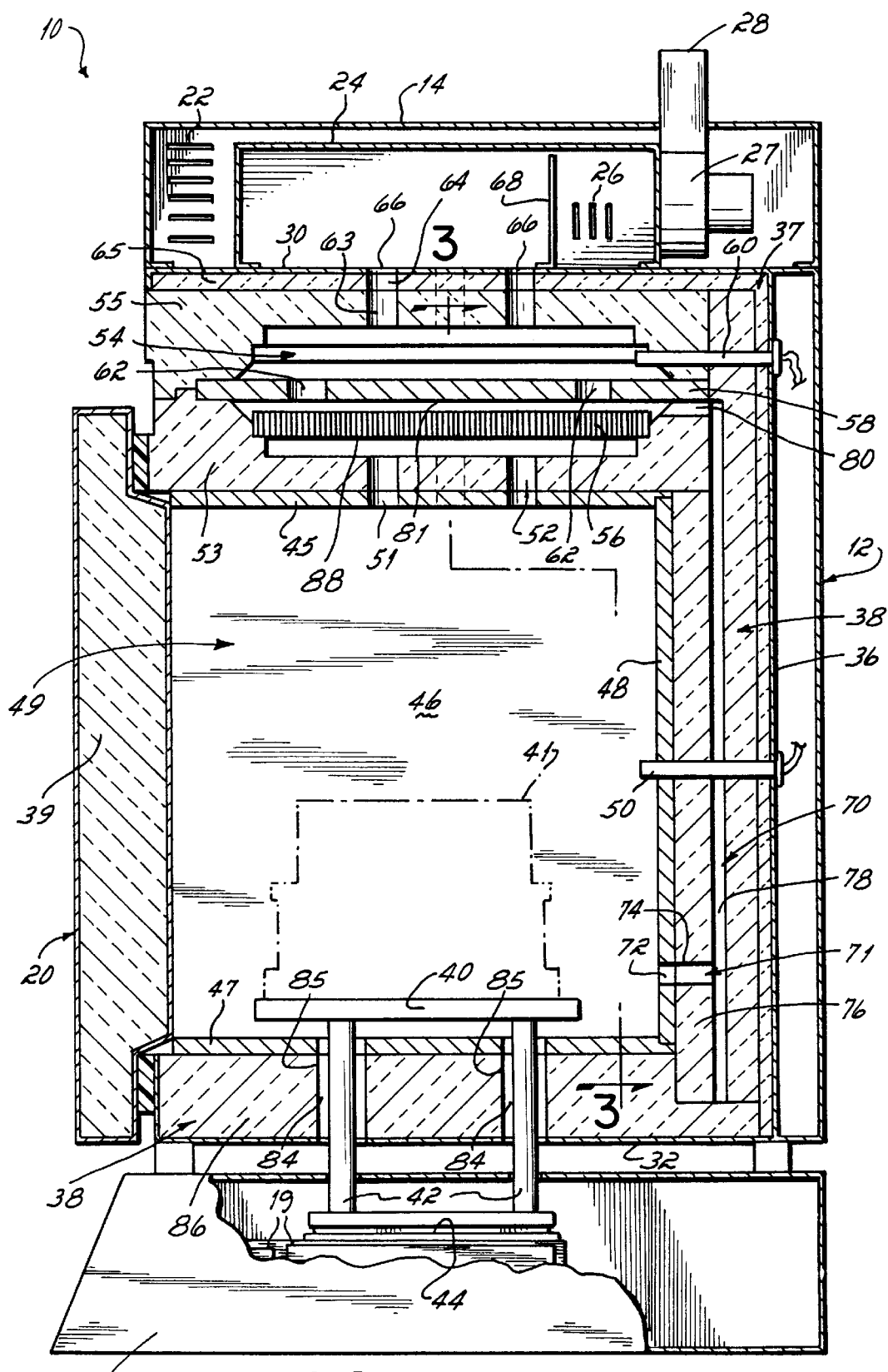
FIG. 2 is a cross-sectional view of the furnace of FIG. 1 taken along line 2—2 of FIG. 1.

Referring now to FIGS. 1–3, enclosure 12 includes a top wall 30, bottom wall 32, a pair of side walls 34 and a rear wall 36. The walls 30, 32, 34 and 36 include a first layer of thermal insulation 37, for example, blanket insulation, disposed on the interior sides of the walls 30, 32, 34 and 36. A second layer of thermal insulation 38, for example, vacuum formed rigid insulation, is disposed inside the blanket insulation 37. Access door 20 also includes thermal insulation 39 on the interior thereof.

A support or hearth plate 40, normally fabricated from silicon carbide, is disposed within the interior of the enclosure 12. Hearth plate 40 is supported on four ceramic posts 42, which themselves are supported by a weigh scale 44, for example, a GT-8000 balance, available from Ohaus, Florham Park, N.J., which provides a readout on panel 18 of the weight of a specimen 41 (shown in phantom) is placed on top of the hearth plate 40 during combustion.

The specimen 41 is heated by a first heater element comprised of a top wall heater plate 45, side wall heater plates 46, and a bottom wall heater plate 47. Each of the heater plates 45, 46 and 47 may be, for example, an alumina heater plate model number EL 1087X1, commercially available from the assignee Barnstead|Thermolyne, Dubuque, Iowa. A rear wall plate 48 is normally made of the same material as the heater plates 45, 46, 47, (with the exception of the element wire), for example, alumina. Thus, the door 20 and wall plates 45, 46, 47 and 48 bound a lower or combustion chamber 49 of the ashing furnace 10. A thermocouple 50 is centrally located in the rear wall plate 48 and extends a short distance into the chamber 49 to sense the temperature in the area adjacent the specimen 41 supported on the hearth plate 40. Thermocouple 50 may be, for example, a TC859X1A, available from the assignee Barnstead|Thermolyne, Dubuque, Iowa. Thermocouple 50 transmits signals to the controller 19 which includes a suitable microprocessor programmed in a known manner with appropriate software, for example, proportional, integral and derivative ("PID") software. The controller 19 provides a PID control for the heater plates 45, 46, 47 and operates solid state relays (not shown) that in turn switch the heater plates 45, 46, 47 ON and OFF to maintain the load 41 at a preselected temperature. For typical asphalt ashing applications, the operating temperature in the area of the load 41 is in the range of approximately 300° C. to 600° C.

Vent holes 51 approximately 1 inch in diameter pass through the heater plate 45 and similarly sized vent holes 52 pass through a first piece of thermal insulation 53, thereby providing a passage between the lower chamber 49 of the furnace 10 and an upper chamber 54. The upper chamber 54 is formed between the first piece of thermal insulation 53 and a second piece of thermal insulation 55. The pieces of insulation 53, 55 are normally identically shaped, vacuum formed, rigid thermal insulation. Mounted within the upper chamber 54 is a gas flow inhibitor or restrictor 56, for example, a reticulated ceramic foam filter or screen. The filter 56 is approximately 0.85 inches thick and has approximately 30 pores per inch, each pore being approximately 0.02 to 0.3 inches in diameter. The filter 56 is commercially available from Selee Corporation, Hendersonville, N.C. An alumina heater plate 58 is mounted above the filter 56 by approximately 0.375 inches. Like heater plates 45, 46 and 47, the heater plate 58 may be, for example, a EL1087X1 commercially available from the assignee Barnstead|Thermolyne of Dubuque, Iowa. The filter 56 functions as a flow restrictor to inhibit or impede the flow of products of combustion from the combustion chamber 49, and such products of combustion include uncombusted products of combustion. For purposes of this application, uncombusted products of combustion are, by definition, larger particles resulting from incomplete combustion and of such a size that their flow is restricted or impeded by the filter 56. The heater plate 58 heats the filter 56; and therefore, the uncombusted products of combustion, produced by the first heater plates 45, 46, 47 and stopped by the filter 56, are burned until they are so reduced in size that they pass through the filter 56 and are further burned by the heater plate 58.

A thermocouple 60 extends into the upper chamber 54 and senses the temperature adjacent the heater plate 58. Like thermocouple 50, thermocouple 60 transmits signals to the controller 19 which operates a solid state relay (not shown) to turn the heater plate 58 ON and OFF, thereby maintaining the upper chamber 54 at a preselected temperature. The thermocouple 60 may be, for example, a TC1087X1 commercially available from the assignee Barnstead|Thermolyne of Dubuque, Iowa. Normally, for ashing applications, the heater plate 58 operates at temperatures in the range from approximately 700° C. to 800° C.

Products of the combustion passing through the filter 56 then pass through vent holes 62 in the heater plate 58, vent holes 63 in the second piece of thermal insulation 55, vent holes 64 in the layer of blanket insulation 65 and vent holes 66 of the top wall 30. The vent hole 62, 63, 64 and 66 are similar in size to the vent holes 51, 52 and provide passages for the products of combustion between the upper chamber 54 and the interior of the inner hood 24. A heat deflector or baffle 68 is mounted above the top wall 30 and facilitates a mixing of the air prior to it entering the inlet of the exhaust fan 27 and exiting the exhaust port 28 of the furnace. The baffle 68 is normally manufactured from stainless steel. Further, the outer hood or housing 14 is spaced from the inner hood 24 to create an insulating space to keep the outer housing 14 at a reasonable temperature.

The furnace 10 further includes a filter bypass path 70 extending from a lower portion of the combustion chamber 49 to a location in the upper chamber 54 between the filter 56 and the heater plate 58. The bypass path 70 has an inlet passage 71 comprised of a vent hole 72 in the rear wall plate 48 and a vent hole 74 in a piece of rear wall thermal insulation 76. The vent holes 72, 74 are approximately 1 inch and 1.25 inches, respectively, in diameter. The inlet passage 71 intersects a ventilation channel 78 that extends vertically through the rear wall thermal insulation 76. The ventilation channel 78 can have any desired cross sectional shape but is normally a rectangular shape with a cross-section that is approximately 2.00 inches by 0.50 inches. The ventilation channel 78 intersects an outlet passage 80 formed in the first piece of thermal insulation 53 which normally has the same cross-section as the channel 78. While the outlet 80 may enter the upper chamber at any point, normally, the outlet 80 enters the upper chamber 80 immediately adjacent the upstream side 81 of the heater plate 58, so that uncombusted materials passing through the outlet 80 are combusted by the heater plate 58. As shown in FIG. 2, the channel 78 is located approximately midway between the centerline and the edge of the rear wall heater plate 48. The exact location of channel 78 is not critical and is chosen to minimize interference with the other components and structure. The vertical location of the inlet passage 71 is lower to minimize the flow of combustion products through the bypass path 70 during combustion at the desired temperature.

In use, the ashing furnace 10 is normally preheated to a desired operating temperature. To initiate the preheating cycle, an operator utilizes the control panel 18 to select the desired temperatures in the combustion chamber 49 and upper chamber 54 that are sensed by the thermocouples 50, 60 respectively. The user then initiates the preheat cycle which causes the heaters 45, 46, 47, 58 to be turned ON and OFF to raise the combustion chamber 49 and upper chamber 54 to the desired selected temperatures. The temperature in the area of the hearth plate 40 is selectable in the range of from 100° C.–650° C., and the temperature is normally selected to be around 550° C. The temperature in the upper chamber 54 is selectable in the range of from 0° C.–900° C. and is normally operated at approximately 750° C. The temperature differential across the filter 56 from its lower, input side to its upper, output side is from approximately 550° C. to approximately 750° C. The actual temperatures of the combustion chamber 49 and upper chamber 54 are displayed to the user by the control panel 18.

Normally the asphalt load is contained in a stainless steel perforated basket (not shown) on a stainless steel tray (not shown) and is preheated to a desired temperature in an oven (not shown) separate from the ashing furnace 10. When the temperature displays on the control panel 18 indicate that the desired preheat temperatures have been reached, the asphalt specimen 41 is placed on top of the hearth plate 40. With the door 20 closed, the blower 27 draws ambient air into the blower hood 14 through slots 22 and into the inner hood 24 through slots 26. In addition, the blower 27 pulls ambient air into the combustion chamber 49 through supply air vents 84 which are annular air passages between the hearth support posts 42 and holes 85 that extend through the bottom heater plate 47, bottom thermal insulation 86 and bottom wall 32. Normally, the products of combustion from the burning asphalt load are pulled by the fan 27 along an exhaust path comprising the holes 51, 52, filter 56, heater plate holes 62 and exit vent holes 63, 64, 66 and discharge vent 28. While some of the combustible material within the sample 41 is fully combusted, uncombusted, that is, incompletely combusted, products of combustion in the form of smoke, soot and ash include heavy carbon organics as well as multiple volatile carbon organics travel upward within the combustion chamber 49 through the passages 51, 52 and against the lower, input side 88 of the filter 56 located in the exhaust path. During the early stages of combustion, especially if the load 41 is large, has a high asphalt content or has a rubberized asphalt content, sufficient quantities of incompletely and uncombusted materials may accumulate on the lower side 88 of the filter 56, that is, in the flow restrictor 56, that flow therethrough 56 is impeded and substantially diminished. However, combustion within the chamber 49 is continuing which continues to heat the gasses therein. In the absence of the filter bypass path 70, a pressure greater than atmospheric pressure may form within the combustion chamber 49 resulting in the gasses within the combustion chamber 49 backflowing through the supply air passages 84. Consequently, some quantities of smoke, soot and ash may be discharged from the ashing furnace into the surrounding environment. Such a condition is irritating to personnel and undesirable.

It is believed that as the smoke, soot and ash backflow through the air inlet passages 84, the flow of combustion air into the combustion chamber 49 is inhibited thereby reducing combustion of the load 41. Consequently, the amount of smoke, soot and ash being produced within the combustion chamber is substantially reduced. At the same time, the smoke, soot and ash continue to burn in the flow restrictor 56 until the particles are diminished in size that they may pass through the flow restrictor 56 and are further combusted by the heater plate 58. The unclogging of the flow restrictor, that is, filter, 56 releases the buildup of gasses within the combustion chamber 49, thereby increasing combustion air flow through the inlet passages 84. The burning or combustion of the load 41 again increases, thereby producing more smoke, soot and ash which again may clog the flow restrictor 56. The above cycle may be repeated several times during the early stages of the combustion cycle.

The filter bypass path 70 shunts the products of combustion around the filter 56, that is, the products of combustion including the smoke, soot and ash, are drawn by the blower 27 into the inlet passage 71, through the ventilation channel 78, out the outlet passage 80 and over the heated lower surface of the heater plate 58. The uncombusted products within the products of combustion are then burned by the heater plate 58 prior to their passing through the holes 62 and out of the upper chamber 54. Therefore, the filter bypass path 70 provides an alternate path for the products of combustion that extends between the combustion chamber 49 and a location downstream of the flow restrictor 56 and adjacent the second heater plate 58. Thus, the further combustion of the products of combustion exiting the bypass path 71 prevents the backflow of smoke, soot and ash through the supply air ventilation holes 84 and promotes the combustion of such products by the heater plate 58 so that they are fully combusted prior to exiting the furnace 10 through the discharge 28.

Once the combustion cycle has reached a steady state condition such that the uncombusted products being discharged from the load 41 can be normally processed by the filter 56, all of the smoke, soot and ash produced from the combustion of the load 41 passes through the filter 56 and heater plate 58. In that normal operating state, the filter bypass path 70 provides combustion air from the lower part of the combustion chamber 49 directly to the upper chamber 54 thereby further promoting combustion of smoke, soot and ash in the upper chamber.

Thus, the filter bypass path 70 has several advantages. First, if the filter 56 should become blocked, the filter bypass path 70 provides a path or shunt for the smoke, soot and ash to be combusted by the heater plate 58 so that it is not discharged directly into the surrounding environment. Second, by promoting the normal flow of gasses through the combustion chamber 49, the flow of combustion air through the inlet channels 84 is not inhibited; and hence, the combustion and temperature of the load will continue at a desirable rate of increase. That has the further advantage of the load reaching the desired combustion temperature and the furnace achieving a steady state condition in the shortest period of time. Thus, the overall cycle time for the furnace is reduced. In addition, during the steady state operation of the furnace, the filter bypass path provides combustion air directly to the upper chamber to further facilitate more complete combustion of the products of combustion passing therethrough.

During the operation of the ashing furnace, the weight of the specimen is continuously monitored and the rate of change of the weight is calculated. The control 19 terminates the test cycle when the rate of change reaches a value that is selectable by the user.

While the invention has been illustrated by the description of one embodiment and while the embodiment has been described in considerable detail, there is no intention to restrict nor in any way limit the scope of the appended claims to such detail. Additional advantages and modifications will readily appear to those who are skilled in the art. For example, the bypass path is described as having a generally quadrilateral cross-section and extending up the rear wall of the combustion chamber. As will be appreciated, the bypass path can have any desired cross-sectional shape, and further it can extend up the side walls. Further, while preferably, the inlet to the bypass path is located lower in the combustion chamber, the inlet may be located at different elevations.

Therefore, the invention in its broadest aspects is not limited to the specific detail shown and described. Consequently, departures may be made from the details described herein without departing from the spirit and scope of the claims which follow.

What is claimed is:

1. A furnace for burning a combustible material comprising:
   a combustion chamber;
   a support within the combustion chamber for supporting the combustible material;
   a first heater element within the combustion chamber for burning the combustible material;
   an exhaust path interconnecting the combustion chamber and an exhaust port communicating with the environment;
   a filter located in the exhaust path and having input and output sides to filter uncombusted products of combustion of the burning combustible material exhausted from the combustion chamber via a portion of the exhaust path between the input side of the filter and the combustion chamber;
   a second heater element disposed in the exhaust path adjacent the output side of the filter for burning the uncombusted products of combustion passing through the filter; and
   a bypass path having an inlet in fluid communication with the combustion chamber and an outlet disposed between the filter and the second heater element, the bypass path shunting the products of combustion from within the combustion chamber around the filter to the second heater element and providing an alternate path between the combustion chamber and a section of the exhaust path downstream of the filter for products of combustion in the event that the filter becomes clogged.

2. The furnace of claim 1 wherein the first heater element is mounted in the combustion chamber above the support.

3. The furnace of claim 1 wherein the combustion chamber has atop wall and the first heater element comprises a first heater plate located at the top wall of the combustion chamber.

4. The furnace of claim 3 wherein the combustion chamber has a bottom wall and two opposed side walls and the first heater element further comprises:
   a second heater plate located at the bottom wall of the combustion chamber; and
   a pair of heater plates each of which is located at one of the two opposed side walls of the combustion chamber.

5. The furnace of claim 2 wherein the filter is disposed above the first heater plate.

6. The furnace of claim 1 wherein the filter is a reticulated ceramic filter having approximately 30 pores per inch, each pore having a diameter of approximately 0.02 to 0.03 inch.

7. The furnace of claim 1 further comprising a chamber located downstream of the combustion chamber and the filter is mounted within the chamber.

8. The furnace of claim 7 wherein the second heater element comprises a heater plate mounted in the chamber downstream of the filter.

9. The furnace of claim 8 further including a first temperature sensor mounted in the combustion chamber and a second temperature sensor mounted in the chamber.

10. The furnace of claim 9 wherein the support is supported atop a plurality of posts which are supported atop the weigh scale, the posts passing through holes in a bottom wall of the furnace, the holes being of a dimension larger than the posts to provide clearance between the posts and holes, the clearance thereby providing an air inlet for combustion of the combustible material.

11. The furnace of claim 10 further including a blower mounted above the chamber, the blower drawing air into the enclosure via the holes.

12. The furnace of claim 1 wherein the furnace includes a rear wall and the bypass path extends through the rear wall.

13. The furnace of claim 12 wherein the inlet opening for the bypass path is disposed in a lower section of the rear wall.

14. The furnace of claim 13 wherein the inlet opening for the bypass path is disposed adjacent the support.

15. The furnace of claim 1 wherein the inlet and outlet of the bypass path are connected by a channel.

16. The furnace of claim 15 wherein the channel extends generally vertically between the inlet and outlet of the bypass path.

17. The furnace of claim 12 wherein the rear wall includes a layer of insulation and the bypass path is formed in the layer of insulation.

18. The furnace of claim 12 wherein the rear wall includes a layer of rigid insulation and the bypass path is formed in the layer of rigid insulation.

19. A furnace for burning a combustible material comprising:
   a combustion chamber having a top wall, a bottom wall, a rear wall, two side walls and an access door;
   a support mounted within the combustion chamber for supporting the combustible material;
   a first heater element comprising a first heater plate mounted at the top wall of the combustion chamber for burning the combustible material;
   an exhaust path interconnecting the combustion chamber and an exhaust port communicating with the environment;

a filter disposed in the exhaust path and having an input and an output with the input in communication with the combustion chamber, the filter filtering uncombusted products of combustion of the burning combustible material exhausting the combustion chamber via the exhaust path;

a second heater element disposed in the exhaust path adjacent the output of the filter for burning uncombusted products of combustion passing through the output of the filter;

a bypass path having an inlet in fluid communication with the combustion chamber and an outlet disposed between the filter and the second heater element, the bypass path shunting the products of combustion from within the combustion chamber around the filter to the second heater and providing an alternative path between the combustion chamber and a section of the exhaust path downstream of the filter for the products of combustion in the event that the filter becomes clogged;

a weigh scale supporting the support, the combustible material thereby being able to be continuously weighed during combustion thereof; and a controller connected to and controlling the operation of the first and second heater elements.

20. The furnace of claim 19 wherein the first heater element further comprises a second heater plate on the bottom wall of the combustion chamber and a pair of heater plates on the opposed side walls of the combustion chamber.

21. The furnace of claim 19 wherein the filter is a reticulated ceramic filter with approximately 30 pores per inch, each pore having a diameter of approximately 0.02 to 0.03 inch.

22. The furnace of claim 19 further including a first temperature sensor in the combustion chamber and a second temperature sensor in the exhaust path.

23. The furnace of claim 19 wherein the support is supported atop a plurality of posts which are supported atop the weigh scale, the posts passing through holes in the furnace bottom wall, the holes being of a dimension larger than the posts to provide clearance between the posts and holes, the clearance thereby providing an air inlet for combustion of the combustible material.

24. The furnace of claim 23 further including a blower mounted above the combustion chamber for drawing air into the combustion chamber via the holes.

25. A furnace for burning a combustible material comprising:

a combustion chamber;

a support within the combustion chamber for supporting the combustible material;

a first heater element within the combustion chamber for burning the combustible material;

a filter having input and output sides and disposed above the support for filtering uncombusted products of combustion of the burning combustible material, the input side of the filter being in fluid communication with the combustion chamber;

a second heater element adjacent the output side of the filter for burning the uncombusted products of combustion passing through the filter; and a bypass path having an inlet in fluid communication with the combustion chamber and an outlet disposed between the filter and the second heater element, the bypass path shunting the products of combustion around the filter to the second heater element and providing an alternative path for the products of combustion from the combustion chamber to the second heater element in the event that the filter becomes clogged.

26. A furnace having upstream and downstream air flow directions and being for use in analyzing materials, said furnace comprising:

an enclosure, a support within said enclosure for supporting a sample including combustible and uncombustible material;

a first heater element adjacent said support for initial combustion of the combustible material of the support;

an uncombusted products flow inhibiting assembly disposed downstream of said first heater element for inhibiting the flow out of said furnace of uncombusted products of the combustible material of the sample;

a second heater element adjacent to and downstream of said uncombustible products flow inhibiting assembly for secondary combustion of the uncombusted products;

a bypass path having an inlet in fluid communication with the enclosure upstream of an inlet of the uncombusted products flow inhibiting assembly and an outlet disposed immediately adjacent the upstream side of the second heater element, the bypass path shunting the products of combustion around the uncombustible products flow inhibiting assembly to the second heater element and providing an alternative path for the products of combustion from the enclosure to the second heater element; and a weight indicating device supporting said support, the sample thereby being able to be weighed before anvil after initial combustion of the combustible material thereof.

27. A furnace for burning a combustible material comprising:

a combustion chamber;

a support within the combustion chamber for supporting the combustible material;

a first heater element within the combustion chamber for burning the combustible material;

a flow restrictor in fluid communication with and disposed downstream of the combustion chamber;

a second heater element having an upstream side directed toward the flow restrictor, the second heater element burning the uncombusted products of combustion passing through the flow restrictor; and a bypass path having an inlet in fluid communication with the combustion chamber upstream of the flow restrictor and an outlet disposed immediately adjacent the upstream side of the second heater element, the bypass path providing an alternative path for the products of combustion from the combustion chamber to the second heater element.

28. A furnace for burning a combustible material comprising:

a combustion chamber bounded by a plurality of walls;

a support within the combustion chamber for supporting the combustible material;

a first heater element within the combustion chamber for burning the combustible material;

an exhaust path interconnecting the combustion chamber with an exhaust port communicating with a surrounding environment;

a second heater element disposed in the exhaust path and having an upstream side directed toward the combustion chamber, the second heater element burning the uncombusted products of combustion exiting the combustion chamber; and a bypass path having an inlet in a wall of the combustion chamber and an outlet disposed immediately adjacent the upstream side of the second heater element, the bypass path providing an alternative path for the products of combustion from the combustion chamber to the second heater element.

29. The furnace of claim 28 wherein the exhaust path includes a flow restrictor for inhibiting the flow of the products of combustion exiting the combustion chamber.

* * * * *

UNITED STATES PATENT AND TRADEMARK OFFICE
CERTIFICATE OF CORRECTION

PATENT NO : 6,033,629
DATED : March 7, 2000
INVENTOR(S) : Friederick et al.

It is certified that error appears in the above-identified patent and that said Letters Patent are hereby corrected as shown below:

Column 8, line 4 reads "atop" and should read --a top--.

Column 10, line 9 reads "enclosure," and should read --enclosure;--.

Column 10, line 34 reads "before anvil after" and should read --before and after--.

Signed and Sealed this

First Day of May, 2001

Attest:

NICHOLAS P. GODICI

Attesting Officer

Acting Director of the United States Patent and Trademark Office